United States Patent [19]

Takeda et al.

[11] Patent Number: 5,252,719
[45] Date of Patent: Oct. 12, 1993

[54] PROCESS FOR PREPARING PROTEIN-ORIENTED MEMBRANE

[75] Inventors: Kazuo Takeda, Kokubunji; Yoshinori Harada, Saitama; Hiromichi Shimizu, Hoya; Chusuke Munakata, Tokyo, all of Japan

[73] Assignee: Hitachi, Ltd., Tokyo, Japan

[21] Appl. No.: 572,595

[22] Filed: Aug. 27, 1990

[30] Foreign Application Priority Data

Aug. 28, 1989 [JP] Japan .................. 1-218583

[51] Int. Cl.[5] .............. C07K 3/08; B05D 5/12; H01L 31/0344
[52] U.S. Cl. .................. 530/409; 136/263; 204/180.2; 250/214.1; 257/40; 257/431; 427/74; 427/338; 530/402; 530/410; 530/810
[58] Field of Search .............. 424/92; 435/170; 530/402, 403, 409, 410, 810; 204/180.2; 250/211 R, 214.1; 357/8; 427/414, 338, 74; 257/40, 431; 430/56, 541, 628; 136/263

[56] References Cited

U.S. PATENT DOCUMENTS

| | | | |
|---|---|---|---|
| 4,582,799 | 4/1986 | Jarvis, Jr. ............... | 435/71.2 |
| 4,613,541 | 9/1986 | Isoda .................... | 427/414 |
| 4,632,800 | 12/1986 | Barraud et al. ........... | 264/298 |
| 4,659,665 | 4/1987 | Freeman et al. .......... | 435/182 |
| 4,804,834 | 2/1989 | Katsura et al. ........... | 250/211 R |
| 5,030,352 | 7/1991 | Varaday et al. .......... | 428/422 |

FOREIGN PATENT DOCUMENTS

| | | |
|---|---|---|
| 0274824 | 7/1988 | European Pat. Off. . |
| 0276782 | 8/1988 | European Pat. Off. . |
| 55-164349 | 12/1980 | Japan . |
| 58-49821 | 11/1983 | Japan . |

OTHER PUBLICATIONS

European Search Report, Apr. 7, 1992, Application No. EP 90116479.

J. Schildkraut, et al., "Purple Membrane and Purple Membrane-Phospholipid Langmuir-Blodgett Films", Thin Solid Films, Dec. 20, 1985, 134:13-26.

T. Furuno, et al., "Photovoltaic Properties of Purple Membrane Langmuir-Blodgett Films", Thin Solid Films, Jun. 1, 1988, 160:145-151.

D. I. Bayramashvili, et al., "Proteinase-Treated Photoreceptor discs. Photoelectric activity of the partially-digested rhodopsin and membrane orientation", Chemical Abstracts, Oct. 8, 1984, 101:266, Column L.

N. W. Downer, et al., "Cross-linking of dark adapted frog photoreceptor disk membranes. Evidence for monomeric rhodopsin", Chemical Abstracts, Nov. 15, 1985, 102:246, Column R.

*Primary Examiner*—Jeffrey E. Russel
*Attorney, Agent, or Firm*—Pennie & Edmonds

[57] ABSTRACT

A process for producing a protein-oriented membrane which is enhanced physically and chemically by orienting protein and cross linking the oriented protein together, is described. The proteinaceous membrane which is subjected to orientation treatment alone is weak physically and chemically, and its processing and handling are therefore difficult. However, according to the present invention, the protein after the process of orientation is cross linked together to produce a protein-oriented membrane remarkably enhanced physically and chemically.

9 Claims, 6 Drawing Sheets

PROCESS FOR PREPARING PROTEIN-ORIENTED MEMBRANE

BACKGROUND OF THE INVENTION

The present invention relates to a process for preparing protein-oriented membrane in biochips for use as solar battery, photo sensor, chemosensor and the like. The present invention further relates to an artificial structure comprising the protein-oriented membrane and a photoelectric transducer produced by using the artificial structure.

Various attempts have been made in order to produce so-called biochips utilizing biological functional protein or biological components containing the same.

As one of such biochips, there have been known those utilizing purple membrane from *Halobacterium halobium* containing a photosensitive protein, bacteriorhodopsin. In the biochips, the component purple membrane is dispersed in a solution, which is then subjected to electrophoresis to form a built-up layer comprising oriented purple membrane on a substrate, namely protein-oriented membrane [see the Preliminary Abstract of 7th *SYMPOSIUM ON FUTURE ELECTRON DEVICES*, 123–127, Nov. 1-2, 1988, Tokyo, Japan].

The conventional process described above has a disadvantage that protein 1 once adsorbed to a substrate 3 is desorbed therefrom when the substrate 3 with the adsorbed protein 1 is exposed to a solvent, as shown in FIG. 5A. Even if the substrate 3 with the adsorbed protein 1 is not exposed to a solvent, the thus obtained protein-oriented membrane was extremely unstable physically. Therefore, it is very hard to handle and process such membrane. In contrast, in the present invention, as shown in FIG. 5B, the proteins 1 which are adsorbed to the substrate 3 are cross-linked with a crossing linking agent 2 to form a stable, oriented and cross-linked protein membrane as shown in FIG. 1B.

In order to solve the drawback, there has been proposed a structure where an oriented purple membrane 6 formed on a substrate 3 is coated with a polymer film 7, as is shown in FIG. 4 (Japanese Patent Laid-open No. 241432/1988). Because output from the membrane 6, such as electric signal and the like, is taken out through the polymer membrane, the reduction in the output cannot be avoided.

Alternatively, as one of those employing other biological components, there has been also proposed another process where proteoliposomes containing rhodopsin as a photosensitive protein similar to the one described above, are two-dimensionally aligned on a substrate, by utilizing antigen-antibody reaction (Japanese Patent Laid-open No.111428/1988). By the process, it is intended only to form a monolayer consisting of proteoliposome on a substrate. It is not intended at all thereby to produce a photoelectric transducer with a high output, by making the layer into multiple ones. According to the process, it is hard to separate only the produced proteinaceous membrane from a substrate, to process the membrane and to connect it with other electrodes.

There has been also known a process comprising interposing a dried membrane of chromatophores between two electrodes (Japanese Patent Laid-open No. 110224/1989), but a structure produced by the process is not satisfactory either, in terms of physical strength and stability against water, concerning the dried membrane.

Other than those described above, there have been known general processes such as a process for fixing functional protein on a substrate using cross linking agents (Japanese Patent Laid-open No. 132954/1990) and a process referred to as the so-called monomolecular sweeping technique comprising forming Langumuir-Blodgett's membrane (referred to as LB membrane) on water surface, transferring the formed LB membrane onto the surface of an aqueous protein solution, and allowing the protein in the aqueous solution to be adsorbed and be oriented spontaneously onto the surface of the LB membrane (Biochim. Biophys. Acta, 225 (1971), pp. 382). According to the former method, the substrate and the protein membrane are strongly bound with each other, but the protein in the membrane is not oriented. Further, the process does not intend to make the protein membrane into a multiple layer. Accordingly, it is difficult to produce a photoelectric transducer with a higher output. It is impossible to separate the protein membrane from the substrate, to process it or to connect it to other electrodes and the like. The latter process has problem in the physical, chemical stability of the protein-oriented membrane thereby produced.

SUMMARY OF THE INVENTION

The present invention has been carried out in order to solve the aforementioned problems proposed by prior art.

The object of the present invention is to provide a modified process for producing a protein-oriented membrane which is provided with excellent physical, chemical stability.

Another object of the present invention is to provide a process for producing a protein-oriented membrane.

Further object of the present invention is to provide a process for producing a protein-oriented membrane, which is capable of producing a multilayer structure composed of a protein-oriented membrane with a high degree of physical strength.

Still another object of the present invention is to provide a photoelectric transducer with a higher output using a multilayer structure composed of a protein-oriented membrane.

Still furthermore object of the present invention is to provide a process for producing a protein-oriented membrane which is provided with excellent processability so that the produced protein-oriented membrane of itself may be taken out, bent, built up and folded.

The present inventors have performed investigations in order to achieve the objects aforementioned. Consequently, they have found that a strong protein-oriented membrane with excellent physical, chemical stability may be produced by orienting protein, and cross linking the oriented protein with each other. Thus, they have achieved the present invention.

That is, the present invention has a characteristic process in the preparation of protein-oriented membrane, such that the protein is oriented and the oriented protein is subsequently cross linked with each other. By cross linking together the oriented protein in such a manner, there may be produced a strong protein-oriented membrane with excellent physical, chemical stability.

The orientation of protein may be effected by allowing the protein to be adsorbed onto a substrate. Adsorption and orientation of protein onto a substrate may be effected utilizing electrophoresis or antigen-antibody reaction. The orientation of proteins may be also effected without a substrate, by forming the Langumuir-Blodgett's membrane of the proteins at the interface of liquid and gas.

The oriented protein may be cross linked with each other, by using a cross linking agent selected from glutaraldehyde, carbodiimide and diamines.

The present invention has another characteristic such that a first layer of protein-oriented membrane is formed by cross linking between the oriented proteins after a first orientation process of protein; a second protein orientation is effected on the protein-oriented membrane as the first layer, and cross linkings between the secondly oriented proteins and between the secondly oriented protein and the protein in the protein-oriented membrane constructing the first layer, to form a protein-oriented membrane as a second layer; the processes described above are repeated, on a needed basis, to form a multilayer structure comprising protein-oriented membranes. By such processes, strong bonding may be accomplished not only within each membrane layer but also between individual membrane layers, so that there may be produced a strong protein-oriented membrane with excellent physical, chemical stability in a multilayer structure.

The present invention has a further characteristic, in that the protein-oriented membrane produced by orienting protein on a substrate and cross linking the oriented protein with each other is flaked from the substrate to produce an isolated protein-oriented membrane, whereby there may be produced a strong protein-oriented membrane which may be isolated for use.

The present invention has another characteristic to provide an artificial proteinaceous structure in monolayer or multilayer, produced by cross linking the oriented protein with each other through a cross linking agent. In the artificial proteinaceous structure, the aforementioned cross linking agent may be a compound selected from glutaraldehyde, carbodiimide and diamines, while the protein may be bacteriorhodopsin or halorhodopsin.

The present invention has further a characteristic to provide an artificial proteinaceous structure in multilayer, produced by cross linking together, with a cross linking agent, bacteriorhodopsin contained in adjacent individual layers in a multilayer which was formed by building up purple membrane containing bacteriorhodopsin.

The present invention has still another characteristic to provide a photoelectric transducer produced by interposing between two electrodes the artificial proteinaceous structure in monolayer or multi-layer, which is obtained in the above manner.

Other characteristics of the present invention, other than those described above, and the advantageous effects thereby obtained will now be sequentially explained in detail in the following Examples.

DESCRIPTION OF PREFERRED EMBODIMENTS

The process of producing a protein-oriented membrane and the structure of the protein-oriented membrane thereby obtained, according to the present invention, will now be explained in detail with reference to the drawings.

The present invention relates to a process for preparing protein-oriented membrane in biochips for use as solar battery, photo sensor, odor sensor, taste sensor and the like. The protein to be used in the present invention includes bacteriorhodopsin, halorhodopsin and the like, which are photoreceptive proteins that are capable of having a non-uniform charge distribution contained in cell membrane of *Halobacterium halobium*. According to the present invention, such protein may be used in the state as it is contained in biomembrane, without isolation. The term protein may be used hereinbelow, including the protein as is contained in biomembrane.

For the preparation of the protein-oriented membrane of the present invention, protein is firstly oriented in a given direction, and the oriented protein is subsequently cross linked with each other.

In the orientation of protein, there may be used for example photoelectrophoresis, antigen-antibody reaction and the technique for forming Langumuir-Blodgett's membrane.

In the utilization of electrophoresis, there may be employed as a substrate, a so-called transparent electrode substrate such as a glass board coated with indium oxide, or the one where polyacrylamide gel or agar gel is formed on the indium oxidecoated glass board.

Figure 6:
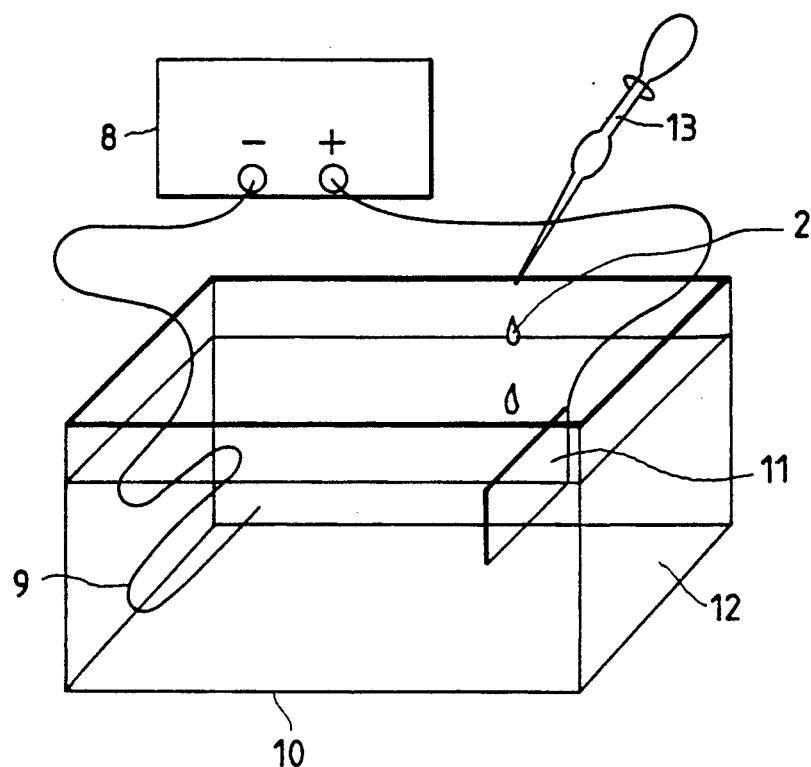
FIG. 6 is a schematic view representing an example of a process for producing a protein-oriented membrane of the present invention, based on the use of electrophoresis.

As is shown for example in FIG. 6, the electrophoresis is performed in the following manner: a transparent electrode substrate 11 as the (+) pole and a platinum electrode 9 as the (−) pole are arranged in an electrophoretic vessel 10 while facing each other, and then a protein suspension 12 is injected into the vessel. Subsequently, a voltage is applied between the two electrodes through a voltage source 8, whereby the protein in the protein suspension is adsorbed onto the surface of the transparent electrode substrate 11, while being oriented by the action of the negative charge and electric dipole moment within the protein molecule. Consequently, a protein-oriented membrane is thus formed on the surface of the transparent electrode substrate 11.

Figure 1A:
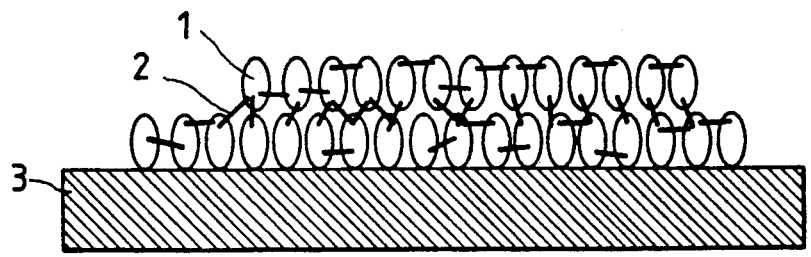
FIGS. 1A, 1B, 1C and 1D are all schematic cross-sectional views representing a constitutional example of the protein-oriented membrane obtained by the process for producing a protein-oriented membrane of the present invention.

Subsequently, a cross linking agent 2 is added through a pipette 13 into the suspension, to cross link together the protein in the protein-oriented membrane formed on the substrate, so that the state of the protein orientation is fixed. The fixed state of orientation is shown in FIG. 1A. The figure shows schematically the manner of how the protein molecule 1 oriented and adsorbed onto the substrate 3 is cross linked with each other through the cross linking agent 2.

A strong protein-oriented membrane in the deposited state on the substrate may be obtained by fixing the orientation state, and taking up the substrate from the suspension and subjecting the substrate to drying process in the above manner.

Figure 7:
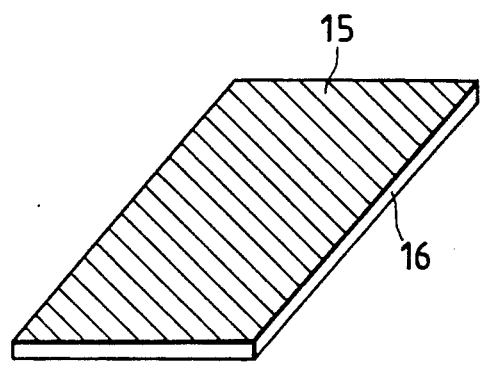
FIG. 7 is a schematic view representing a structure of a protein-oriented membrane, formed on a transparent electrode, according to the process of the present invention.

According to the present invention, an electrophoretic solution containing a new suspension of protein is firstly prepared, and then the same procedure described above is repeated using the substrate which has the protein-oriented membrane constituted by cross linking the protein on its surface, in order to form a multilayer comprising the protein-oriented membrane, so that there may be produced a thick layered membrane where the adjacent protein-oriented membranes are cross linked together. FIG. 7 shows a protein-oriented membrane 15 thus layered and formed on a substrate (transparent electrode) 16.

Figure 3:
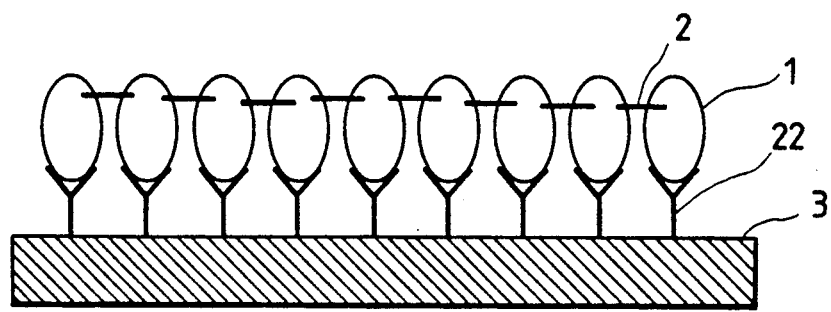
FIG. 3 is a schematic cross-sectional view representing a still other constitutional example of the protein-oriented membrane obtained by the process for producing a protein-oriented membrane of the present invention.
Figure 4:
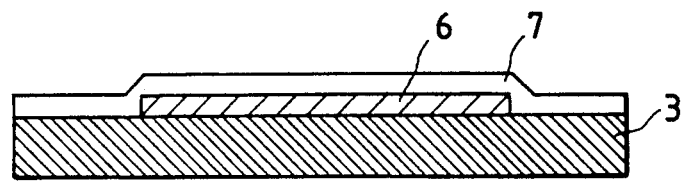
FIG. 4 is a schematic cross-sectional view representing a typical constitutional example of a protein-oriented membrane by prior art.

In case an antigen-antibody reaction is utilized, an antibody against a protein to be oriented is prepared and the antibodies are developed on a solution such as Ringer's solution, to form a monolayer of the oriented antibodies. Subsequently, the monolayer is transferred to the substrate, and soaked in the protein suspension for promoting antigen-antibody reaction to orient the protein on the substrate. Furthermore, by adding a cross linking agent to cross link together the oriented protein and finally drying the cross-linked product, a cross linked membrane comprising the oriented proteins may be obtained. The present state is schematically shown in FIG. 3. As is shown in the figure, the oriented protein molecule 1 is cross linked together through the cross linking agent 2, as well as being bound onto the substrate 3 with the antibody 22.

Figure 1B:
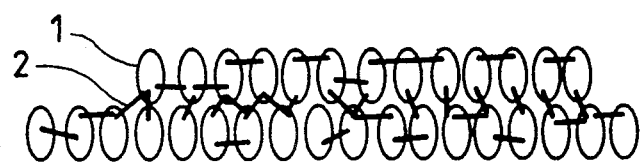

The protein-oriented membrane obtained by these procedures is strongly bound with each other, but the bonding between the substrate and the protein-oriented membrane is weak. Accordingly, the protein-oriented membrane can be flaked from the surface of the substrate. A cross-sectional view representing the membrane in such state is shown in FIG. 1B. In the figure, 1 represents a protein molecule and 2 represents a cross linking agent.

In case an electrophoresis is used, a protein-oriented membrane may be flaked from a substrate, far more easily, by employing the following method.

According to the method, there may be used a liquid with a larger density than that of a protein suspension, such as glycerin. The upper layer of the (+) electrode arranged on the lower portion of a electrophoretic vessel is covered with a liquid such as glycerin, to carry out orientation and cross linking at the interface between the suspension and the liquid such as glycerin. There may exist a liquid such as glycerin and the like between the protein-oriented membrane obtained by the present method and the substrate, so that the protein-oriented membrane can be flaked from the substrate far more easily.

According to the present invention, there may be employed a method where Langumuir-Blodgett's membrane forming at an interface between liquid and gas is used, with no use of a substrate.

Figure 2:
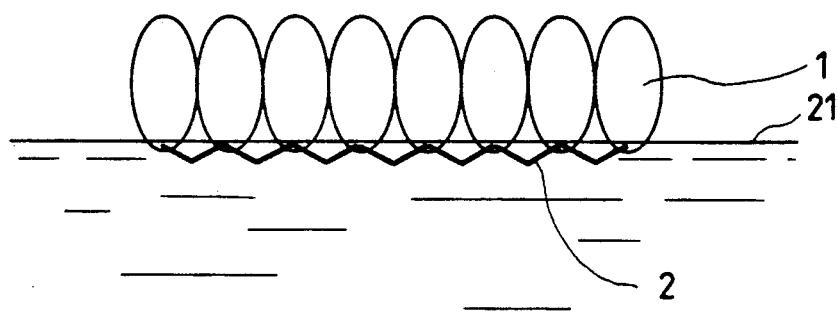
FIG. 2 is a schematic cross-sectional view representing another constitutional example of the protein-oriented membrane obtained by the process for producing a protein-oriented membrane of the present invention.

In the method, protein is suspended in an appropriate solvent with a polarity different from that of water, for example, hexane, which is then spread on the surface of distilled water. The protein is oriented thereby toward a given direction corresponding to its polarity (see Biochimica et. Biophysica Acta, Vol.509 (1978) p.300; Thin Solid Films, 160 (1988) 145), to form a protein-oriented membrane. The state is shown in FIG. 2. In the figure, 21 represents water surface, 2 represents a cross linking agent, and 1 represents a protein molecule oriented. The protein-oriented membranes formed by the method can be built up in any number.

Figure 1C:
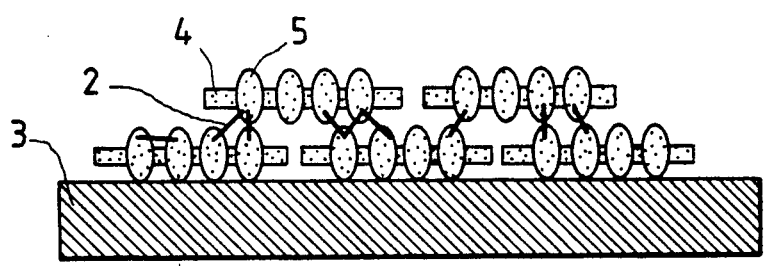
Figure 1D:
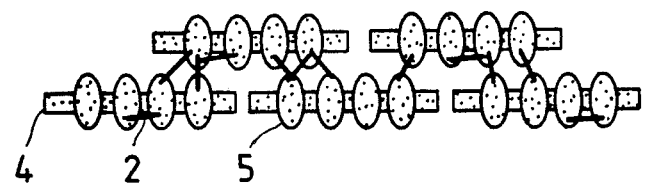

According to the present invention, an oriented membrane can be prepared by the same procedure as described above, using the protein as is contained in membrane fragments such as cell membrane or membrane of organella. As is shown in FIG. 1C, the process therefor comprises orienting membrane protein 5 in a membrane fraction 4, allowing the oriented membrane protein 5 being adsorbed onto a substrate 3, and cross linking the membrane protein 5 with each other through a cross linking agent 2 to link together the membrane fractions 4, whereby a stable oriented membrane having a large surface area may be formed. The oriented cross linking membrane may be flaked and isolated singly from the substrate, as is shown in FIG. 1D. FIG. 1D shows a cross-sectional view of the oriented cross-linking membrane composed of membrane fractions 4 stably cross-linked together by oriented membrane proteins 5 which are cross-linked with a cross linking agent 2.

The cross linking agent of the present invention to be used in the above processes may be one which can cross link protein together. There is no specific limitation concerning the agent, and it includes for example glutaraldehyde, carbodiimide and diamines.

In case of producing a photoelectric transducer according to the present invention, for example, a protein-oriented membrane is prepared by using, as protein, a functional protein such as bacteriorhodopsin, halorhodopsin and the like. The protein-oriented membrane thus obtained may be used as a photoelectric transducer, by being connected to the (−) electrode in the same manner as has been in practice conventionally, while the element is adsorbed onto a transparent electrode substrate. According to the present invention, it is possible to flake and take out only the protein-oriented membrane from its substrate for subjecting to processing, as is described above. In particular, the membrane can be connected to an electrode other than the substrate which is used to form the membrane.

Figure 8:
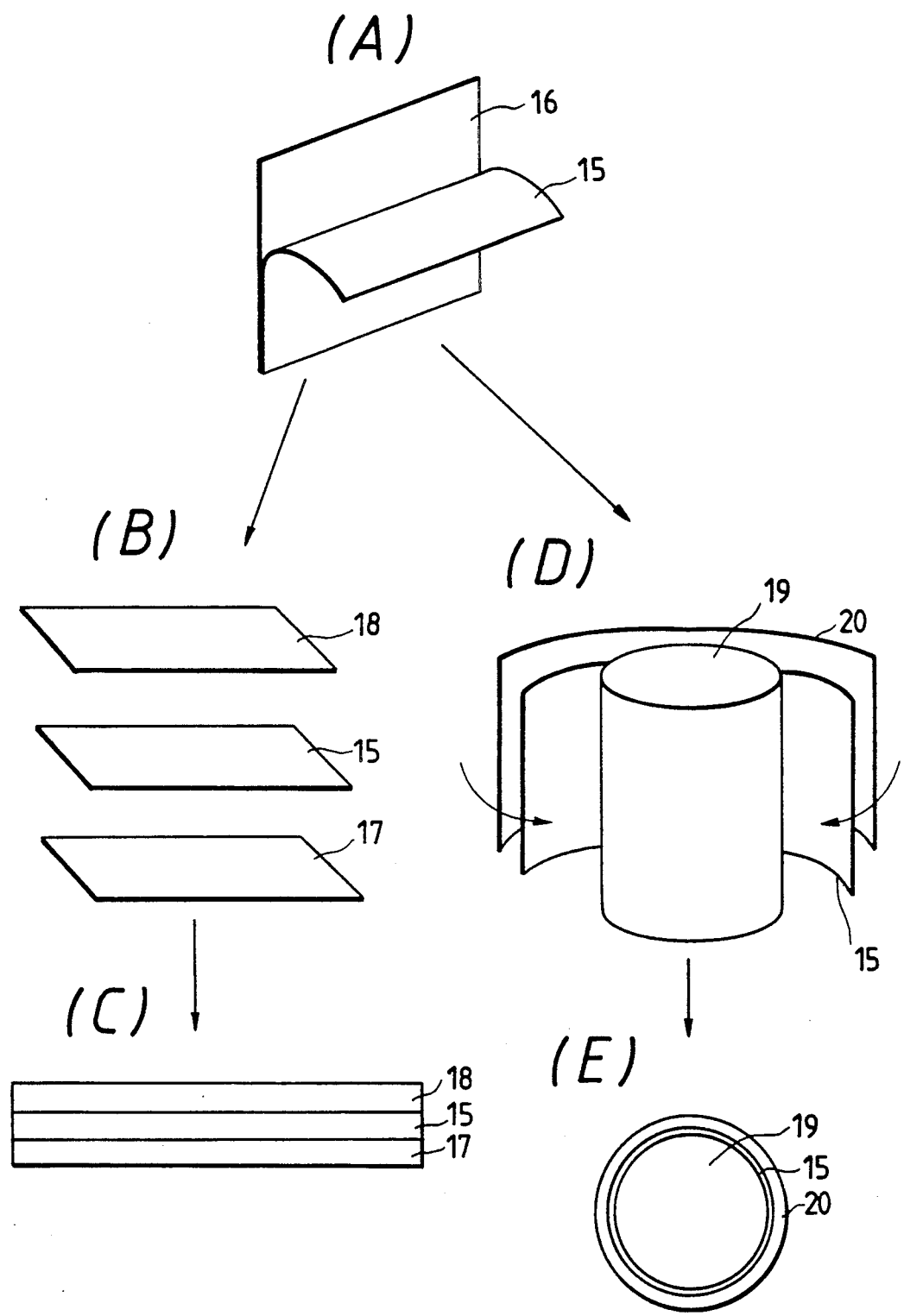
FIG. 8 is a process view representing the process for producing a photoelectric transducer, according to the process of the present invention.

FIG. 8 shows schematically what is described immediately above; photoelectric transducers in a wide variety of forms may be obtained by flaking the protein-oriented membrane 15 of the present invention from a substrate 16 (FIG. 8A), interposing the flaked protein-oriented membrane 15 between plane electrode substrates 18, 17 (FIGS. 8B and C), or winding the protein-oriented membrane 15 and an electrode 20 comprising flexible materials around a cylindrical electrode 19 (FIGS. 8D and E).

Figure 5A:
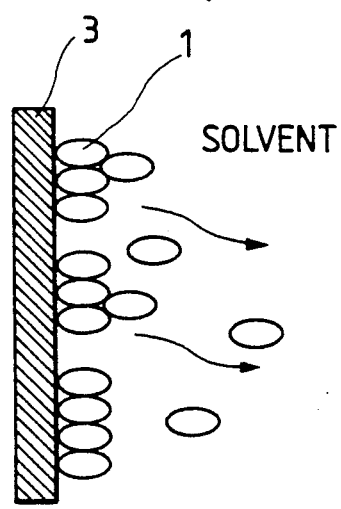
FIG. 5A is a schematic cross-sectional view representing the manner how a protein-oriented membrane obtained by prior art is desorbed from its substrate into a solvent.
Figure 5B:
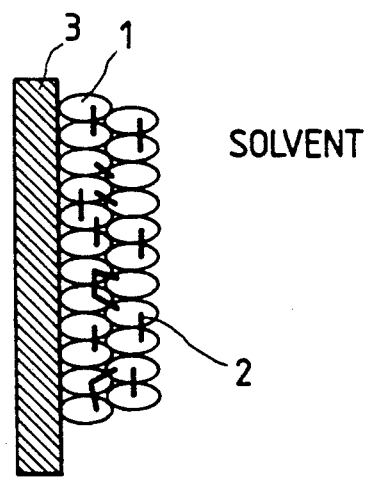
FIG. 5B is a schematic cross-sectional view representing that the protein-oriented membrane produced by the process of the present invention is insoluble in solvent.

Because in the protein-oriented membrane of the present invention the proteins are fixed together through cross linking with a cross linking agent as is shown in FIG. 5B, the membrane thus gets insoluble in a solvent such as water and the like, giving the great physicochemical stability to the protein-oriented membrane.

Those adjacent protein-oriented membranes which are cross linked together and built up may be further stabilized physicochemically. Use of functional proteins including bacteriorhodopsin, halorhodopsin and the like may produce a photoelectric transducer with an high output. Furthermore, the protein-oriented membrane of the present invention may be flaked from the substrate 16 while keeping the form of membrane as is shown in FIG. 8A, and may be subjected to various processing modes such as connecting to electrodes in a variety of forms (FIGS. 8B, C, D and E).

Specific Examples of the present invention will now be illustrated below, but the present invention is not merely limited to them.

EXAMPLE 1

Purple membrane was suspended in water adjusted at pH 6.0 to 9.0. A transparent electrode (glass coated with indium oxide) (+ side) and a platinum electrode (− side) were arranged and soaked in 50 cc of the solution, interposing the interval 4 cm between the two electrodes. While applying a 5 V voltage to the electrodes over 10 hours, electrophoresis was performed until the purple membrane charged negative was thoroughly adsorbed to the transparent electrode on the (+) side. Subsequently 0.1 cc of a solution of 20% glutaraldehyde was added dropwise and application of the voltage was continued for additional 10 hours. Finally, the transparent electrode was taken out from the electrophoretic solution and dried to obtain a transparent electrode on which was deposited the oriented cross linking membrane of purple membrane. FIG. 1C shows schematically an expanded sectional view of a build-up layer comprising purple membrane fractions, formed on the transparent electrode.

After the electrophoretic solution containing a suspension of purple membrane was prepared, the same procedure aforementioned was repeated using the substrate on which the oriented cross linking membrane was formed, whereby was formed a membrane with a certain thickness and in a layered structure in which the adjacent oriented cross-linking membranes were linked together through cross linking among the proteins.

EXAMPLE 2

A transparent electrode board was put at the bottom of a vessel and then, a certain amount of a polyacrylamide solution of a few % to 15% was poured into the vessel up to a few mm higher than the upper surface of the transparent electrode board. Then, the board was left to stand for several hours until completion of polymerization. Subsequently, the polymerized polyacrylamide gel was cut off to take out the transparent electrode board. Purple membrane was suspended in water adjusted at pH 6.0 to 9.0. The transparent electrode covered with the polyacrylamide gel layer (+side) and a platinum electrode (−side) were arranged and soaked in 50 cc of the solution, interposing the interval 4 cm between the two electrodes. While applying a 5 V voltage to the electrodes over 10 hours, electrophoresis was performed until the purple membrane charged negative was thoroughly adsorbed to the transparent electrode on the (+) side. Subsequently 0.1 cc of a solution of 20% glutaraldehyde was added dropwise and application of the voltage was continued for additional 10 hours to promote the cross linking reaction. Finally, the transparent electrode was taken out from the electrophoretic solution and dried to obtain a transparent electrode adsorbing the oriented cross linking membrane of purple membrane.

EXAMPLE 3

Agar gel membrane of a 1 mm thickness was formed on a transparent electrode board, using a 1.5% agar gel solution.

On the other hand, purple membrane was suspended in water adjusted at pH 6.0 to 9.0. The transparent electrode covered with the agar gel layer (+side) and a platinum electrode (−side) were arranged and soaked in 50 cc of the solution, interposing the interval 4 cm between the two electrodes. While applying a 5 V voltage to the electrodes over 10 hours, electrophoresis was performed until the purple membrane charged negative was thoroughly adsorbed to the gel on the transparent electrode on the (+) side. Subsequently 0.1 cc of a solution of 20% glutaraldehyde was added dropwise and application of the voltage was continued for additional 10 hours to promote the cross linking reaction. Finally, the transparent electrode was taken out from the electrophoetic solution and dried to obtain a transparent electrode adsorbing the oriented cross linking membrane of purple membrane.

EXAMPLE 4

Purple membrane was suspended in water adjusted at pH 6.0 to 9.0. A transparent electrode (+side) was arranged at the bottom of a vessel into which was poured 50 cc of the solution, and soaked therein while interposing the interval 4 cm from a platinum electrode (−side). While keeping the temperature of the solution at 10° C. or less, 100% glycerin was subsequently injected into the solution up to the height of a few mm to a few cm above the surface of the transparent electrode. Then, the 5 V voltage was applied between the electrodes, and electrophoresis was carried out until the purple membrane charged negative was aligned at the interface of glycerin and water. Ater 0.1 cc of a solution of 20% glutaraldehyde was subsequently added dropwise to the above solution, cross linking reaction was effected under the application of the voltage for 10 hours, to form an oriented cross linking membrane at the interface of glycerin and water. The oriented cross linking membrane could be flaked readily from the substrate.

EXAMPLE 5

A part of the carboxyl terminal of bacteriorhodopsin (the part from Glu of the 232th amino acid residue to Ser of the 248th amino acid residue at the carboxyl terminal) is hydrophilic and protrudes outside into a solution from the inside of the protein itself. The antibody produced against the part was dissolved in Ringer's solution (an aqueous solution comprising 0.85 wt % NaCl, 0.014 wt % KCl, 0.012 wt % $CaCl_2$ and 0.012 wt % $NaHCO_3$) at a concentration of 1 mg/ml and spread over an aqueous solution containing 110 mM NaCl, 2 mM KCl, 1.8 mM $CaCl_2$, 20 wt/vol % sucrose to form a monolayer comprising the antibody over the water surface. In the monolayer comprising the antibody, its binding site with the antigen is sequenced downward due to the polarity of the antibody. By the plane deposition technique, the monolayer was transferred to a substrate through hydrophobic treatment (a transparent substrate after soaking in an octadecyl trichlorosilane solution and drying). The substrate on which was formed the molecular membrane of the antibody in such manner, was immersed in the Ringer's solution suspended with purple membrane to promote the antigen-antibody reaction. Subsequently, the substrate was taken up from the liquid surface and soaked in an aqueous solution of 0.004% glutaraldehyde, to promote the cross linking reaction. Finally, the substrate was taken up from the liquid surface and dried, to obtain a transparent electrode onto which was adsorbed the oriented cross linking membrane comprising purple membrane.

The oriented cross linking membrane formed in the above manner is shown in FIG. 3. The figure represents the state such that the protein as antigen is sequenced and fixed with a cross linking agent, while the antibody 22 is sequenced on a substrate 3. In the Example, the substrate, the protein as antigen and the cross linking agent 2 correspond to a transparent electrode, bacteriorhodopsin and glutaraldehyde, respectively.

EXAMPLE 6

The hexane solution suspended with purple membrane at a concentration of 0.5 mg/ml was spread over distilled water to form a Langumuir-Blodgett's (LB) membrane comprising purple membrane over the water surface. The LB membrane aligns along a given direction, corresponding to the polarity of purple membrane. To the water with the LB membrane floating therein was subsequently added 20% glutaraldehyde at a concentration of 0.4% and left to stand at room temperature for one hour in order to effect the cross linking reaction to form an oriented cross linking membrane of purple membrane over the water surface. The oriented cross linking membrane thus formed was then taken out and dried to obtain a purple membrane-adsorbing oriented membrane.

EXAMPLE 7

After purple membrane was oriented on a transparent substrate following the same procedure as in Example 1, a solution of 1.0M 1-ethyl-3-(3'-dimethyl aminopropyl)-carbodiimide-HCl (prepared in 1M borate buffer (pH 9.0)) was added to an electrophoretic solution, instead of 0.1 cc of 20% glutaraldehyde, and then left to stand at room temperature for one hour while applying a 5 V voltage. Finally the transparent electrode as a substrate was taken out from the electrophoretic solution and dried to obtain an oriented cross linking membrane of purple membrane.

EXAMPLE 8

After purple membrane was oriented on a transparent substrate following the same procedure as in Example 1, a solution of 1.0M (3,3'-diamino)dipropylamine (prepared in 1M borate buffer (pH 9.0)), instead of 0.1 cc of 20% glutaraldehyde, was added to an electrophoretic solution and then left to stand at room temperature for one hour while applying a 5 V voltage. Finally the transparent electrode as a substrate was taken out from the electrophoretic solution and dried to obtain an oriented cross linking membrane of purple membrane.

EXAMPLE 9

Figure 9A:
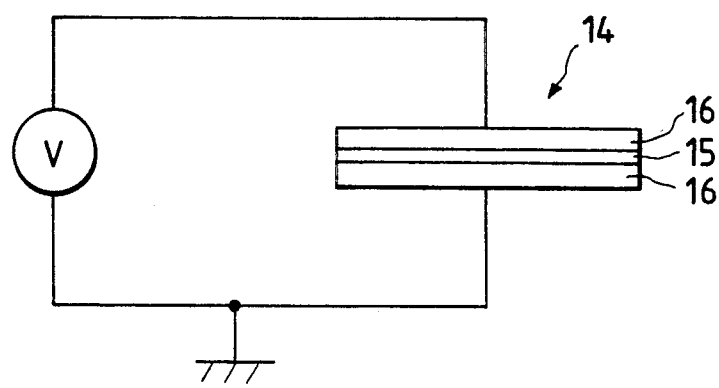
FIG. 9A is a circuit chart representing a constitution of a detecting circuit for detecting photoelectrostatic signals on the protein-oriented membrane obtained by the process of the present invention.
Figure 9B:
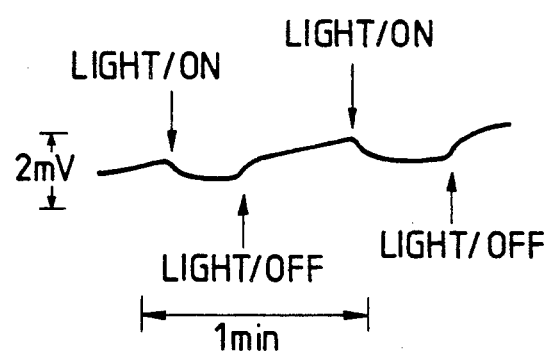
FIG. 9B is a wave form chart representing an example of the detected photoelectrostatic signals.

As is shown in FIG. 9A, the purple-membrane oriented cross linking membrane layer 15 on the transparent electrode, formed in Example 1, was additionally covered with a transparent electrode 16. Water was allowed to immerse into the purple-membrane-oriented cross linking membrane layer to prepare a detecting circuit of photovoltaic signal. The results of irradiation of light 14 were such that the photovoltaic signals of about 1 mV were produced by irradiation of He-Ne laser (1 mW), in case of the purple-membrane-oriented cross linking membrane layer of a 30 um thickness. The raw data are shown in FIG. 9B. The figure shows how the photovoltaic output signals changed when the irradiation of light 14 was turned on and off.

As has been demonstrated in the above description, the protein-oriented membrane obtained according to the present invention is extremely stable physicochemically, because the protein is strongly cross linked together; the membrane is sufficiently strong, particularly in a solvent such as water and the like. Physicochemical stability of those in which the protein-oriented cross linking membrane is cross linked together through the cross linking of the proteins in the membranes is more enhanced, which may realize to produce a photoelectric transducer with a high output.

Furthermore, the protein-oriented cross linking membrane may be taken out from the substrate and handled singly, so that it may be processed in various ways and connected to a variety of other electrodes. The membrane may be applied in extremely wide fields.

The performance of the photoelectric transducer using the artificial structure comprising the protein-oriented membrane of the present invention is extremely excellent. Accordingly, the present invention provides remarkably useful and dramatic effects in the development and application in biochips.

What is claimed is:

1. A process for producing a protein-oriented membrane comprising the steps of:
   orienting photoreceptive protein molecules that are capable of having a non-uniform charge distribution;
   cross linking the oriented protein molecules together to form said protein-oriented membrane.

2. The process for producing a protein-oriented membrane according to claim 1, wherein said protein molecules are oriented by adsorbing said protein molecules onto a substrate.

3. The process for producing a protein-oriented membrane according to claim 2, wherein said protein molecules are adsorbed onto said substrate by electrophoresis.

4. The process for producing a protein-oriented membrane according to claim 2, wherein said protein molecules are adsorbed onto said substrate by an antigen-antibody reaction.

5. The process for producing a protein-oriented membrane according to claim 1, wherein said protein molecules are oriented by forming a Langumuir-Blodgett's membrane with said protein molecules at the interface between liquid and gas.

6. The process for producing a protein-oriented membrane according to claim 1, wherein said oriented protein molecules are cross linked with a cross linking agent.

7. The process for producing a protein-oriented membrane according to claim 6, wherein said cross linking agent is selected from the group consisting of glutaraldehyde.

8. The process for producing a protein-oriented membrane according to claim 6, wherein said cross linking agent is carbodiimide.

9. The process for producing a protein-oriented membrane according to claim 6, wherein said cross linking agent is a diamine.

* * * * *